United States Patent [19]

Chu et al.

[11] Patent Number: 5,384,396
[45] Date of Patent: Jan. 24, 1995

[54] PROCESS FOR THE DEOXYGENATION OF NUCLEOSIDES

[75] Inventors: Chung K. Chu, Athens, Ga.; Yaoquan Chen, Shanghai, China

[73] Assignee: The University of Georgia Research Foundation, Inc., Athens, Ga.

[21] Appl. No.: 665,751

[22] Filed: Mar. 7, 1991

Related U.S. Application Data

[63] Continuation-in-part of Ser. No. 318,694, Mar. 3, 1989, abandoned, which is a continuation-in-part of Ser. No. 159,246, Feb. 23, 1988, abandoned.

[51] Int. Cl.[6] .............................................. C07H 19/00
[52] U.S. Cl. ........................... 536/27.14; 536/27.21; 536/28.1; 536/28.2
[58] Field of Search ................... 536/23, 24, 26, 27, 536/28, 29, 27.1, 27.21, 27.14, 28.2

[56] References Cited

U.S. PATENT DOCUMENTS

| | | | |
|---|---|---|---|
| 3,282,921 | 11/1966 | Verheyden, et al. | 536/28.2 |
| 3,687,931 | 8/1972 | Verheyden, et al. | 536/27.14 |
| 3,755,295 | 8/1973 | Verheyden, et al. | 536/28.55 |
| 3,775,397 | 11/1973 | Etzold, et al. | 536/28.2 |
| 4,071,680 | 1/1978 | Cook | 536/28.52 |
| 4,078,139 | 3/1978 | Barton et al. | 536/17 |
| 4,230,698 | 10/1980 | Bobek, et al. | 514/49 |
| 4,604,382 | 8/1986 | Lin, et al. | 514/49 |
| 4,788,181 | 11/1988 | Driscoll et al. | 536/23 |
| 4,904,770 | 2/1990 | Starrett, Jr., et. al. | 536/27.14 |
| 4,921,950 | 5/1990 | Wilson | 536/28.54 |

FOREIGN PATENT DOCUMENTS

| | | |
|---|---|---|
| 8523878 | 9/1985 | Great Britain . |
| 8603447 | 2/1986 | Great Britain . |
| 86301897.4 | 10/1986 | Europe . |
| 86307071.0 | 4/1987 | Europe . |

OTHER PUBLICATIONS

Chu et al., *J. Org. Chem.*, v. 54, pp. 217–2225, (1989).
Anzai, et al., *Agri. Biol. Chem.* 37(2), 345 (1973).
Barrett, et al., *J.C.S. Chem. Comm.* 866 (1977).
Barrett, et al., *J.C.S. Perkin I* 2378 (1979).
Classon, et al., *Acta Chemica Scandinavica* B36, 251 (1982).
Colla, et al., *Eur. J. Med. Chem.—Chim. Ther.* 20(4), 295 (1985).
Chem. Abstract 101:192378c (1984).
Chem. Abstract 96:69346s (1982).
Chem. Abstract 105:227205f (1986).
Dyatkina, *Sovie J. Biorg. Chem.* 12, 563 (1986).
Heredewijn, et al., *J. Med. Chem.* 30, 1270 (1987).
Horton, et al., *J. Org. Chem.* 35, 10 (1970).
Horowitz, et al., *J. Am. Chem. Soc.* 86, 1896 (1964).
Horowitz, et al., *J. Org. Chem.* 29, 2076 (1984).
Horowitz, et al., *J. Org. Chem.* 31, 205 (1966).
Horowitz, et al., *J. Org. Chem.* 32, 817 (1967).
Horowitz, et al., *Tet. Letters* 1343 (1966).

(List continued on next page.)

Primary Examiner—Johnnie R. Brown
Assistant Examiner—James O. Wilson
Attorney, Agent, or Firm—Kilpatrick & Cody

[57] ABSTRACT

An efficient process for the deoxygenation of 2'- and or 3'-hydroxyl groups of a nucleoside that includes reacting the hydroxyl group with 3-halopropionitrile or 2-nitroethylhalide and carbon disulfide in base to form a 2'- or 3'-(cyanoethylthio or nitroethylthio)thiocarbonyl, that is reductively eliminated and replaced with hydrogen. The deoxygenation process can be used in a wide variety of nucleoside syntheses that require the elimination of the 2'- or 3'-hydroxyl groups, including the preparation of 3'-substituted-2',3'-dideoxynucleosides such as 3'-azido-3'-deoxythymidine and 3'-azido-2',3'-dideoxyuridine.

18 Claims, 4 Drawing Sheets

OTHER PUBLICATIONS

Jain, et al., *J. Org. Chem.* 39, 30 (1974).
Lin, et al., *Biochem. Pharmacol.* 36, 2713 (1987).
Lin, et al., *J. Med. Chem.* 30, 440 (1987).
Lin, et al., *J. Med. Chem.* 21(1), 109 (1978).
Lin, et al., *J. Med. Chem.* 26, 1691 (1983).
Lin, et al., *J. Med. Chem.* 26, 544 (1983).
Krenitsky, et al, *J. Med. Chem.* 26(6), 891 (1983).
McCarthy, et al., *J. Am. Chem. Soc.* 88, 1549 (1966).
Prisbe and Martin, *Synthec Communications* 15(5), 401, (1985).
Robins, et al., *Tet. Letters* 25, 367 (1984).
Russell, et al., *J. Am. Chem. Soc.*, 95, 4025 (1973).
Tong, et al., *J. Org. Chem.* 30, 2854 (1965).
Webb, et al., *Nucleosides and Nucleotides* 7(2), 147 (1988).
Nakayama, et al., *Nucleosides & Nucleotides*, 1(2), 139-146 (1982).
Codington, et al., *J. Am. Chem. Soc.*, 82 (1960).
Yung, et al., *J. Am. Chem. Soc.*, 83, 3065 (1961).
Fox, et al., *J. Am. Chem. Soc.*, 78 (1956).
Horton, et al. *Carbohydrate Research*, 48 (1976).
Holy, et al., *Collection of the Czechslovak Chem. Commun.*, 39 (1974).
Paquette, et al., *J. Org. Chem.*, 56(3), 912 (1991).

PROCESS FOR THE DEOXYGENATION OF NUCLEOSIDES

This is a continuation-in-part of U.S. Ser. No. 07/318,694, entitled "Method of Synthesis of 2',3'-Dideoxy and 2',3'-Dideoxydidehydro Nucleosides," filed on Mar. 3, 1989, by Chung K. Chu, now abandoned, that is a continuation-in-part of U.S. Ser. No. 07/159,246, entitled "2',3'-Dideoxynucleosides as Anti-Retroviral Compositions and Their Method of Preparation," filed on Feb. 23, 1988 by Chung K. Chu and Raymond F. Schinazi, now abandoned.

BACKGROUND OF THE INVENTION

This invention is in the area of synthetic organic chemistry, and is in particular an efficient, cost effective process for the deoxygenation of the 2'-or 3'-position of a nucleoside that avoids N-alkylation. 2'- or (3'-) Deoxynucleosides prepared according to this method can be used as intermediates in the manufacture of a wide range of synthetic nucleoside derivatives, including the pharmaceutically important 3'-substituted-2',3'-dideoxynucleosides A nucleoside is a molecule consisting of a 5-carbon sugar and a purine or pyrimidine base. Addition of a phosphate group to the 5' position of the nucleoside converts the nucleoside into a nucleotide. Natural nucleotides are the building blocks for the nucleic acids, RNA (ribonucleic acid) and DNA (deoxyribonucleic acid).

In 1985, it was reported that the synthetic nucleoside 3'-azido-3'-deoxythymidine (AZT) inhibits the replication of human immunodeficiency virus type 1 (referred to below as HIV). Mitsuya, H., et al., *Proc. Natl. Acad. Sci. U.S.A.* 82, 7096 (1985). HIV is believed to cause acquired immunodeficiency syndrome (AIDS). Since then, a number of other 3-substituted-2',3'-dideoxynucleosides having anti-HIV activity have been identified, including 3'-azido-2',3'-dideoxyuridine (referred to as AZDU, or CS-87), 3'-azido-2',3'-dideoxycytidine (CS-91), 3'-azido-5-methyl-2',3'-dideoxycytidine (CS-92), 5-ethyl-3'-azido-2',3'-dideoxyuridine (CS-85), and 3'-fluoro-3'-deoxythymidine (FDT).

Deoxynucleosides have historically been prepared by either of two routes; condensation of a deoxy sugar moiety with a nitrogenous base, or deoxygenation of a preformed nucleoside.

Synthetic schemes for the preparation of nucleoside derivatives from preformed nucleosides include those described by: Dyatkina, N. B., *Soviet J. Biorg. Chem.* 12, 563 (1986); Colla, et al., *Eur. J. Med. Chem. - Chim. Ther.* 20(4), 295 (1985); Herdewijn, et al., *J. Med. Chem.* 30, 1270 (1987); Horowitz, et al., *J. Org. Chem.* 29, 2076 (1984); Krenitsky, et al., *J. Med. Chem.* 26(6), 891 (1983); and Webb, et al., *Nucleosides and Nucleotides* 7(2), 147 (1988).

The original syntheses of 3'-azido and 3'-amino analogs of 2',3'-dideoxythymidine, 2',3'-dideoxycytidine, and 2',3'-dideoxyuridine were reported by Lin and Mancini in 1983. Lin, T. S., and Mancini, W. R., *J. Med. Chem.* 26, 544 (1983). The first step in the Lin scheme is the mesylation of the 3'-position of 5'-protected thymidine or 2'-deoxyuridine. Treatment with base provides the 2,3'-anhydro nucleoside derivative, that is acidified and again mesylated to form the 1-[2-deoxy-3-O-methanesulfonyl-5-O-(protected)-β-D-threopentofuranosyl]nucleoside. This compound is then reacted with azide ion and deprotected to produce a 3'-azido-3'-deoxythymidine or 3'-azido-2',3'-dideoxyuridine. 3'-Azido-2',3'-dideoxycytidine was prepared by converting the pyrimidine carbonyl of 3'-azido-2',3'-dideoxyuridine to an amino function. The 3'-amino analogs were prepared by reduction of the 3'-azido moieties.

While the Lin and Mancini reaction scheme is suitable for the industrial preparation of 3'-substituted-2',3'-dideoxynucleosides, it is limited because the starting material, 2'-deoxynucleoside, is difficult to obtain and expensive. For example, AZT was originally prepared from thymidine that was isolated from herring sperm, available in only limited quantities.

Prisbe and Martin, in *Synthetic Communications,* 15(5), 401–409 (1985), disclose a method for the preparation of 2',3'-dideoxynucleosides by the deoxygenation of a 5'-O-acetyl-2'-deoxynucleoside. The deoxygenation step was carried out by reacting the 3'-hydroxyl group of the nucleoside with N,N-thiocarbonyldiimidazole, followed by treatment with methanol to yield the corresponding methylthionocarbonate. Reduction of the thionocarbonate with tri-n-butyl tin hydride provided the desired 2',3'-dideoxynucleoside The procedure is not suitable for manufacturing scale because N,N-thiocarbonyldiimidazole is prohibitively expensive and the thionocarbonate is difficult to purify before reduction.

Robins, et al., *J. Am. Chem. Soc.,* 103, 932–933 (1981) disclose that nucleoside thionocarbonates can be prepared in a single step with phenoxythiocarbonyl chloride. Reduction of the thionocarbonate with tri-n-butyl-tin hydride provides the desired deoxynucleoside. This process is not suitable for manufacturing scale because phenoxythiocarbonyl chloride is very expensive.

Most of the other reported methods of preparation of nucleosides by derivatization of preformed nucleosides are suitable only as laboratory syntheses to obtain small amounts of compound for experimental use, but are not well suited for industrial scale preparation of the compounds, because of the number of steps required to obtain the product and the cost of the nucleoside starting material.

Synthetic schemes for the preparation of nucleoside derivatives that include the step of condensing a sugar with a nitrogenous base are described in a number of publications, including U.S. Pat. No. 4,921,950 to Wilson, U.S. Pat. No. 4,230,689 to Bobek, et al; Fleet, Son and Drome, *Tetrahedron* 42(2), 625 (1988); and European Patent Application No. 86307071.0 filed by the Wellcome Foundation, Limited.

As with preformed nucleosides, nucleosides prepared by condensing a sugar with a base typically contain hydroxyl groups at the 2' and or 3'-positions of the nucleoside that must be removed to provide the final 2',3'-dideoxynucleoside product.

Deoxygenation of some nucleosides can be accomplished by treating the nucleoside with an excess of carbon disulfide and an alkyl halide to form a 2'- and or 3'-bis(OC(S)(S)alkyl) derivative (referred to as a xanthate derivative) that can be deoxygenated with tributyltin hydride. The advantage of this method is that the reagents used to prepare the xanthate are inexpensive and readily available. However, it has been discovered by Chu, et al., (see *J. Org. Chem.,* 54, 2217, 2218–2219 (1989), and U.S. Ser. No. 07/318,694) that when certain 5=O-protected ribonucleosides are treated with an excess of carbon disulfide and an alkyl halide to form the xanthate derivative, the isolated product includes nucleoside that has been alkylated at the $N_1$ position of purine or $N_3$ position of pyrimidine. The undesired N-alkylation significantly reduces the efficiency of the reaction, and increases the cost of the final product.

The problems described above that are encountered in the preparation of pharmaceutically active nucleosides increase the cost of health care and result in shortages of severely needed antiviral compounds. Further, the high cost of the antiviral, and in particular anti-HIV, nucleosides prevents many of those in need from being able to obtain the drug.

In light of this, there is a strong need for an efficient process to deoxygenate the 2' or 3'-position of a nucleoside that does not result in N-alkylation of the nucleoside in the process. In particular, there is a need for a preparation of 3'-substituted-2',3'-dideoxynucleosides, notably 3'-azido-2',3'-dideoxyuridine and 3'-azido-3'-deoxythymidine, that has a minimal number of steps and a high yield of product.

It is therefore an object of the present invention to provide a process for the deoxygenation of the 2' or 3'-position of a nucleoside that does not result in undesired N-alkylation.

It is another object to provide a process for the preparation of 3'-substituted-2',3'-dideoxynucleosides that is efficient and convenient.

SUMMARY OF THE INVENTION

An efficient process is provided for the deoxygenation of the 2'- and or 3'-hydroxyl groups of a nucleoside. The process includes reacting the hydroxyl group with 3-halopropionitrile or 2-nitroethylhalide ($XCH_2CH_2CN$ or $XCH_2CH_2NO_2$, respectively, wherein X is chloro, bromo, or iodo), and carbon disulfide in base to form a 2' or 3'-cyanoethylxanthate or nitroethylxanthate, that is reductively eliminated and replaced with hydrogen.

The reductive elimination can be carried out with a catalyst such as triethylborane or azobisisobutyronitrile (AIBN) and a reducing agent such as tris(trimethyl silyl)silane or tri-n-butyltin hydride. Tri-n-butyltin hydride can be generated inexpensively in situ from tri-n-butyltin chloride and sodium borohydride, but is typically used at elevated temperatures. Tris(trimethylsilyl)silane and triethylborane can be used at ambient temperatures, minimizing undesired side reactions and in some cases increasing the yield of product. For example, 1-[3,5-O-Isopropylidene-2-O-(cyanoethylthio)thiocarbonyl-$\beta$-D-xylofuranosyl]thymine (compound 8, FIG. 1) can be reduced with triethylborane and tris(-trimethylsilyl)silane at ambient temperature to provide 1-(3,5-O-isopropylidene-$\beta$-D-2-deoxyxylofuranosyl)thymine (compound 9, FIG. 1) in 93% yield. The same reaction can be performed with AIBN and tri-n-butyltin hydride at 90° C. to provide compound 9 in 86% yield.

The process described here is superior to the prior art methods of deoxygenating the 2' and or 3'-positions of the nucleoside in that it does not cause undesired N-alkylation of the heterocyclic base of the nucleoside. The process can be used in the preparation of a wide variety of nucleosides, including thymidine, inosine, cytidine, uridine, guanosine, and adenosine derivatives. Another advantage of this process is that it employs inexpensive reagents that are readily available. 3-Chloropropionitrile and 3-bromopropionitrile are less expensive than the prior used thiocarbonyldiimidazole or phenoxythiocarbonyl chloride.

The deoxygenation process can be used in a wide variety of nucleoside syntheses that require the elimination of the 2' or 3'-hydroxyl groups, including the preparation of 3'-substituted-2',3'-dideoxynucleosides, 2'-deoxynucleosides, and 2'-substituted-2',3'-dideoxynucleosides. The process can be used with any type of sugar incorporated into a nucleoside, including xylose and ribose, or with sugars not attached to heterocyclic bases.

In a preferred process, 3'-substituted-2',3'-dideoxynucleoside is prepared by: (1) condensing a derivatized xylose with a heterocyclic base to form a 1-(2,3,5-trisubstituted-$\beta$-D-xylofuranosyl)pyrimidine nucleoside; (2) converting the nucleoside to a 1-[3,5-O-isopropylidene-2-O-(cyanoethylthio or nitroethylthio)thiocarbonyl-$\beta$-D-xylofuranosyl]pyrimidine; (3) reducing the product of step 2 to form a 1-(3,5-O-isopropylidene-$\beta$-D-deoxyxylofuranosyl)pyrimidine; and then (4) derivatizing the 3'-position of the nucleoside as desired. Reduction (step 3) is carried out with tri-n-butyltin hydride and azobisisobutyronitrile at reflux in an organic solvent or with triethylborane and tris(trimethylsilyl)silane at ambient temperature. Both 3'-azido-2',3'-dideoxyuridine and 3'-azido-3'-deoxythymidine can be prepared in high yield in this manner without undesired N-alkylation.

BRIEF DESCRIPTION OF THE FIGURES

FIG. 1 is a schematic illustration of a process for the preparation of 3'-azido-3'-deoxythymidine ("AZT").

FIG. 2 is a schematic illustration of a process for the preparation of 3'-azido-2',3'-dideoxyuridine ("AZDU").

DETAILED DESCRIPTION OF THE INVENTION

The term "3'-substituted nucleoside" as used herein refers to a nucleoside in which the hydroxyl group in the 3'-position has been replaced by another functional group, including but not limited to azido, amino, alkoxy, organosulfonyloxy, halogen, or hydrogen.

A process is disclosed for the deoxygenation of 2' or 3'-hydroxyl groups from nucleosides that includes three key steps. The progress of these reactions can be monitored with thin layer chromatography. First, the protected nucleoside is reacted with carbon disulfide in base to form a 2' or 3'-OC(S)S(—) derivative. Suitable bases are known to those skilled in the art, and include NaOH, KOH, and NaH. This reaction is preferably carried out at a temperature range of between approximately 0° and 60° C., and typically takes from about ten minutes to six hours to complete. In the second step, 3-halopropionitrile or 2-nitroethylhalide is added to the reaction mixture in situ to form a 2' or 3'-O-(cyanoethylthio or nitroethylthio)thiocarbonyl. This reaction is preferably carried out at a temperature range of between approximately 0° and 50° C., and typically takes from about thirty minutes to five hours to complete. In the third step, the (cyanoethylthio or nitroethylthio)thiocarbonyl is reductively removed to provide a 2' or 3'-hydrogen moiety. Reduction can be effected with a catalyst such as triethylborane or azobisisobutyronitrile (AIBN) and a reducing agent such as tris(trimethyl silyl)silane or tri-n-butyltin hydride. Tri-n-butyltin hydride is typically used in an organic solvent at reflux, whereas triethylborane and tris(trimethyl silyl)silane can be used at ambient temperature.

This process for the deoxygenation of the 2' or 3' position of a nucleoside is a significant improvement over the prior art processes, because it results in a high yield of product and does not cause permanent N-alkylation of the heterocyclic base. It appears that the heterocyclic ring nitrogens may be transiently alkylated by halopropionitrile or 2-nitroethylhalide in base to form a N—CH$_2$CH$_2$CN or N—CH$_2$CH$_2$NO$_2$ group. The base then abstracts a hydrogen from the ethyl group to form NCH$_2$CH(—)CN or NCH$_2$CH(—)NO$_2$, that quickly eliminates acrylonitrile or nitroethylene, returning the heterocycle to its unalkylated state. In contrast, a simple alkyl halide such as methyl iodide is used in place of halopropionitrile or 2-nitroethylhalide, a stable N-alkyl nucleoside is formed, decreasing the yield or preventing the formation of any useful product.

The halogen moiety in halopropionitrile or nitroethylhalide can be bromo, chloro, or iodo. The brominated reagents are preferred because they are more active than the chlorinated reagents. The iodinated reagents are the most active, but easily participate in side reactions, including photochemical reactions, and are unstable.

The hydroxyl groups in the sugar moiety of the nucleoside that are not to be deoxygenated should be protected during the reaction. Suitable protecting groups are known to those skilled in the art. Examples of suitable protecting groups include without limitation, 2-O-silyl groups such as t-butyldimethylsilyl, t-butyldiphenyl silyl, 1,1,3,3-tetraisopropyldisilox-1,3-diyl, benzyl, trityl, methoxytrityl, methoxybenzyl, and other substituted benzyl and substituted trityl moieties. Acyl protecting groups can be used if the process is performed under anhydrous conditions and a base such as NaH used in the deoxygenation step.

When the 2'-position of a ribofuranosyl nucleoside is to be deoxygenated, 1,1,3,3-tetraisopropyldisilox-1,3-diyl is particularly useful for simultaneous protection of the 3' and 5' hydroxyl groups. When the 2'-position of a xylofuranosyl nucleoside is to be deoxygenated, the 3'-and 5' hydroxyl groups are preferably protected by an alkylidine group such as isopropylidine or benzylidine. Alkylidine groups can be added by reacting the nucleoside with an aldehyde such as benzaldehyde or a ketone such as acetone in the presence of an acid catalyst. Other suitable protecting groups include benzyl or substituted benzyl groups or trityl or substituted trityl groups.

One of skill in the art can incorporate the deoxygenation process described herein into a wide variety of synthetic schemes, including the preparation of 2'-deoxynucleosides, such as 2-Cl-2'-deoxyadenosine (see generally Carson, et al. Proc. Natl. Acad. of Sciences USA, 81, 2232, 1984), and 2'-substituted-2',3'-dideoxynucleosides (see Watanabe, *J. Med. Chem.* 2145 (1990)), given the description of the process provided here. The deoxygenation process can also be used to deoxygenate sugars, including ribose and xylose, that have not been condensed with a base.

Below are nonlimiting examples for the preparation of 3'-azido-3'-deoxythymidine and 3'-azido-2',3'-dideoxyuridine from xylose that incorporate this deoxygenation process. The process from xylose to xylouridine or xylothymidine has been reported by Nakayma and Saneyoshi, Nucleosides & Nucleotides, 1, 139–146 (1982). For ease of illustration, bromopropionitrile is used as the reagent for derivatization of the 2'-position. These reaction schemes can be easily modified by one of skill in the art for the use of chloropropionitrile, iodopropionitrile, or nitroethylhalide.

In the working examples below, melting points were determined on a Thomas Hoover capillary apparatus and are not corrected. $^1$H NMR spectra were recorded on a JEOL FX 90Q spectrometer using Me$_4$Si as internal standard. Chemical shifts are reported in ppm ($\delta$) and signals are quoted as s (singlet), d (doublet), t (triplet), q (quartet), or m (multiplet). UV spectra were obtained on a Beckman DU-7 spectrophotometer. IR spectra were recorded on a Nicolet 510P FT-IR spectrometer. Optical rotations were determined on a JASCO DIP-730 Digital Polarimeter. TLC was performed on Uniplates (silica gel) purchased from Analtech Co. Elemental analyses were performed by Atlantic Microlab Inc., Norcross, GA. Anhydrous acetonitrile was purchased from Aldrich Chemical Company and other dry solvents were obtained by drying over 4Å molecular sieves.

EXAMPLE 1

Process for the Preparation of 3'-Azido-3'-Deoxythymidine

Figure 1A:
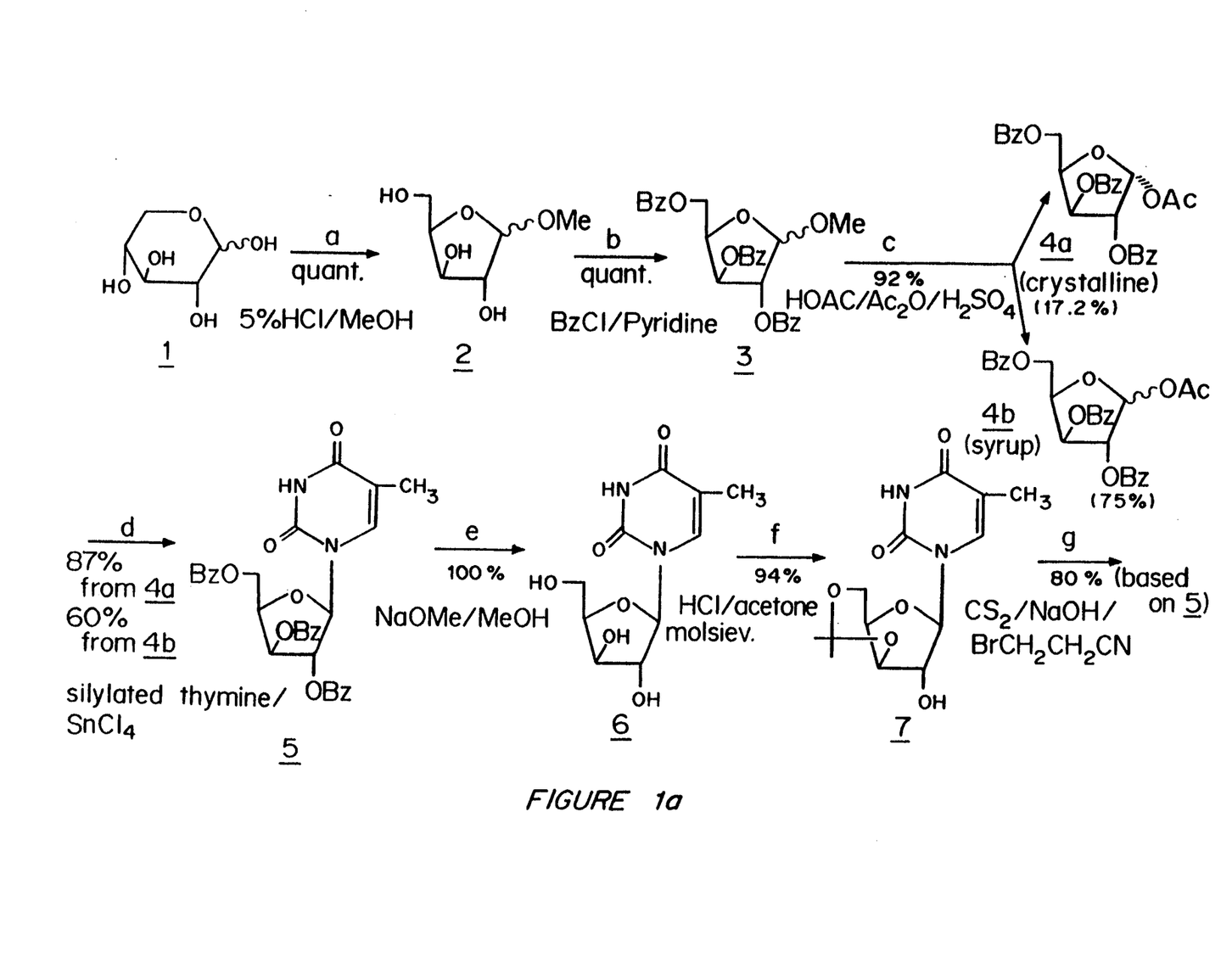
Figure 1B:
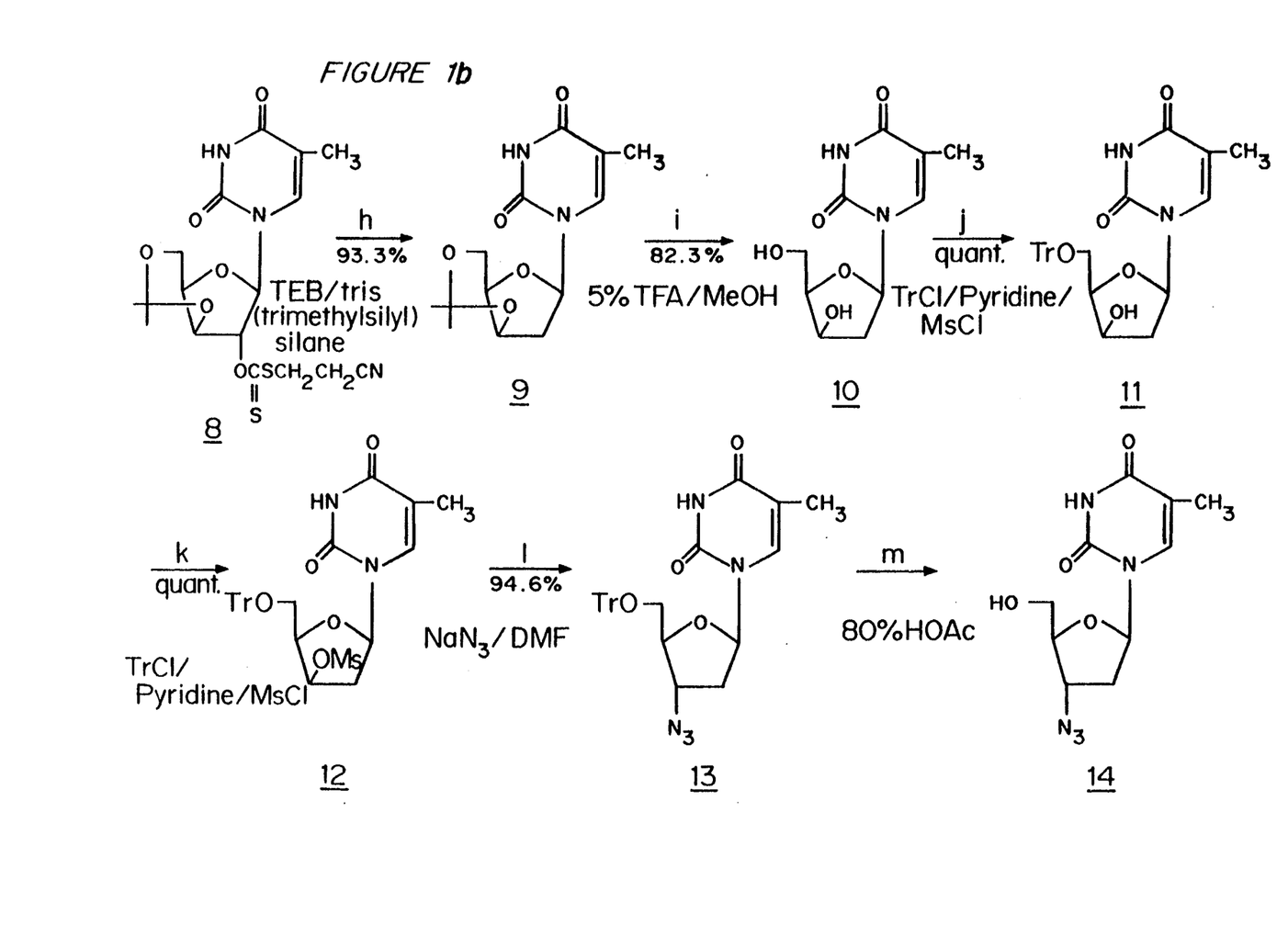

FIG. 1 is an illustration of a process for the preparation 3'-azido-3'-deoxythymidine from D-xylose that incorporates the step of deoxygenating the 2'-position of the nucleoside by reductive elimination of a 2-O-(cyanoethylthio)thiocarbonyl-$\beta$-D-xylofuranosyl]thymine group.

Xylose is initially converted to the corresponding 2,3,5-tri-O-protected-1-substituted derivative. The 1-position should be derivatized to a group that can be easily eliminated and replaced with a desired heterocyclic base. A preferred moiety is 1-O-acetyl, that can be prepared by mixing the corresponding 1-O-methyl-D-xylose with acetic acid or acidic anhydride. Other suitable groups are known to those skilled in the art, and include halo and alkoxy. The halide can be prepared by reacting the xylose-1-O-acetate with hydrogen chloride or bromide. These reactions can be monitored for completeness with TLC.

As shown in FIG. 1, D-xylose (compound 1) was converted to 1-methoxy-2,3,5-tri-O-benzoyl-xylose (FIG. 1, compound 3) in quantitative yield in two steps. Compound 3 was reacted with a mixture of acetic acid and acetic anhydride in sulfuric acid to obtain 1-acetyl-2,3,5-tribenzoyl-D-xylose 4a (17.2%, the $\alpha$ anomer) and 4b (75%, a mixture of the $\alpha$-anomer and the $\beta$-anomer). The crystalline compound 4a can be separated from the 4b mixture.

In the next step of this reaction scheme, the 1-acetyl-2,3,5-tri-O-benzoyl xylose is condensed with a protected base in the presence of a Lewis acid or trimethylsilyl triflate (trimethylsilyl trifluoromethanesulfonate) in a dry organic solvent.

Friedel-Crafts catalysts (Lewis acids) that can be used in the condensation reaction include SnCl$_4$, ZnCl$_4$, TiCl$_4$, AlCl$_3$, FeCl$_3$, BF$_3$-diethyl ether, and BCl$_3$. These catalysts require anhydrous conditions because the presence of water reduces their activity. The catalysts are also inactivated in the presence of organic solvents with active hydrogens, such as alcohols and organic acids. The catalysts are typically used in solvents such as carbon disulfide, methylene chloride, nitromethane, 1,2-dichloroethane, nitrobenzene, tetrachloroethane, chlorobenzene, benzene, toluene, dimethylformamide, tetrahydrofuran, dioxane, or acetonitrile. Anhydrous aluminum chloride is not soluble in carbon disulfide. Niedballa, et al., *J. Org. Chem.* 39, 3654 (1974). The preferred catalyst is SnCl₄. Preferred solvents are acetonitrile and 1,2-dichloroethane.

Trimethylsilyl triflate can be used under the same conditions described above for the Friedel-Crafts catalysts. The reaction proceeds at a temperature range of from −10° C. to 200° C.

The choice of catalyst for condensation will affect the final product ratio of α to β nucleoside product (the β-anomer is desired). For example, SnCl₄ typically provides a higher ratio of β to α anomer than trimethylsilyl triflate.

As shown in FIG. 1, 1-(2',3',5'-tri-O-benzoyl-β-D-xylofuranosyl)thymine 5 was obtained in 87% yield by reacting silylated thymine with the crystalline intermediate 4a, in the presence of SnCl₄, while a 60% yield of the same compound was obtained from 4b under the same conditions.

The three benzoyl groups of 1-(2',3',5'-trio-O-benzoyl-β-D-xylofuranosyl)thymine can be removed by treatment with basic reagents such as sodium methoxide or methanolic ammonia. Sodium methoxide is preferred here because when methanolic ammonia is used, benzamide is produced, that is difficult to separate from the desired product. Methanolic ammonia is satisfactory for deprotection of the corresponding uracil analog.

Isopropylidenation of 1-(β-D-xylofuranosyl)thymine 6 to 1-[3,5-O-isopropylidene β-D-xylofuranosyl]thymine 7 was carried out in high yield (94%).

The key feature of this scheme is the elimination of the 2'-hydroxyl group from the nucleoside in a manner that does not result in N-alkylation of the heterocyclic base. In this scheme, this is accomplished through the use of carbon disulfide and 3-halopropionitrile in base to form a 2'-O-(cyanoethylthio)thiocarbonyl moiety, that was reductively eliminated to the corresponding 2'-hydrogen group. As shown in FIG. 1, compound 7 was treated with CS₂/NaOH followed by 3-bromopropionitrile to obtain 1-[3,5-O-isopropylidene-2-O-(cyanoethylthio)thiocarbonyl-β-D-xylofuranosyl]thymine (compound 8). Reduction of compound 8 with tris(trimethylsilyl)silane provided a high yield of 1-(3,5-O-isopropylidene-β-D-2-deoxyxylofuranosyl)thymine (compound 9) (93.3%).

The isopropylidene protecting group of compound 9 was then removed, and the 5'-O-hydroxyl group tritylated, to provide 1-(5-O-trityl-β-D-2-deoxyxylofuranosyl)thymine (compound 11). The 3'-azido group was introduced to compound 11 using the method of Lin, T. S., and Mancini, W. R., *J. Med. Chem.* 26, 544 (1983).

The preparation of 3'-azido-3'-deoxythymidine is further illustrated in the following working examples. Compounds are numbered as illustrated in FIG. 1.

1-Acetyl-2,3,5-tribenzoyl-D-xylose (4)

A suspension of D-xylose (1) (90 g, 0.6 mol) in methanol (1500 mL) containing 0.5% (w/w) hydrogen chloride was stirred at room temperature for 5 hours. The resulting clear solution was neutralized with solid sodium bicarbonate and filtered. The filtrate was evaporated and co-evaporated in vacuo with dry pyridine to give a syrup, compound 2, that was redissolved in pyridine (600 mL). To the ice-cooled solution of compound 2 in pyridine, benzoyl chloride (270 mL, 2.34 mol) was added dropwise while stirring. The solution was stirred at room temperature overnight, and then concentrated in vacuo. The resulting residue was partitioned between ethyl acetate and water. The aqueous phase was extracted with ethyl acetate. The combined organic phases were washed with aqueous sodium bicarbonate, and then water, and dried over anhydrous sodium sulfate. The resulting dark solution was decolorized with active charcoal and concentrated to give compound 3 as a pale yellow syrup (372.5 g). This product was dissolved in a mixture of acetic acid (480 mL) and acetic anhydride (120 mL), and cooled in an ice-water mixture. Concentrated sulfuric acid (75 mL) was then added dropwise with stirring. The mixture was stirred at room temperature overnight, treated with sodium acetate (120 g) and then evaporated in vacuo to dryness. The residue was partitioned between ethyl acetate and water. The organic phase was washed with aqueous sodium bicarbonate and water, and dried over sodium sulfate. Evaporation of this solution gave a thick syrup (321.2 g) that was crystallized from hot methanol (1 L) to give viscous white needles. The needles were recrystallized from hot methanol (1 L) to give white needles. The product was collected by filtration and washed with methanol, and then dried to give 51.8 g of the α-anomer (17.2%). The combined mother liquor and washings were evaporated to a give pale yellow syrup (226.4 g, 75.0%) that contained both α- and β-anomers, with the α-anomer as the major component. Melting point of the crystalline α-anomer, 127.0°–128.2° C. (lit 124°–126° C., 127°–128.5° C.). $[\alpha]_D^{24}$ 149.9° (c, 0.57, CHCl₃) (lit. $[\alpha]_D^{14}$=154° (c, 1.2, CHCl₃) (lit. $[\alpha]_D^{31}$=+147° (c, 1.0 CHCl₃). ¹H NMR (CDCl₃) δ2.05 (s, 3H, OAc), 4.55 (d, 2H, H-5, $J_{5,4}$=5.05 Hz) 4.88–5.05 (m, 1H, H-4), 5.79 (dd, 1H, H-3, J=4.40, 5.74 Hz), 6.09 (t, 1H, H-2, J=6.38 Hz), 6.70 (d, 1H, H-1, $J_{1,2}$=4.62 Hz), 7.27–8.10 (m, 15H, Bz).

1-(2,3,5-Tribenzoyl-β-D-xylofuranosyl)thymine (5)
Method A: with crystalline sugar 4a To an ice-cooled mixture of crystalline 4a (50 g, 99.2 mmol) in anhydrous acetonitrile (450 mL) and silylated thymine (prepared from 14.24 g of thymine) tin (IV) chloride (15 mL) was added dropwise with stirring. After stirring at room temperature for 48 hours, the mixture was neutralized with a mixture of ice and solid sodium bicarbonate and then filtered. The filter cake was washed with hot ethyl acetate. The combined filtrate and washings were evaporated to give a pale yellow solid that was partitioned between ethyl acetate and water (1 liter of each). The white solid was collected by filtration, washed with ethyl acetate and water, and then dried to give a solid (38.9 g). The organic phase was washed with water (4×500 mL), dried over sodium sulfate, and evaporated to a give pale yellow solid, which was recrystallized from hot methanol to give a white solid (11 g). Total yield was 49.9 grams (87%). mp 199.8°–200.9° C. (lit. 198°–199° C.). $[\alpha]_D^{24}$ 63.5 (c, 0.51, CHCl₃) ¹H NMR (DMSO-d₆) 1.73 (s, 3H CH₃), 470–5.05 (m, 3H, H-4' and 5'), 5.74 (m, 1H, H-3'), 5.95 (m, 1H, H-2'), 6.22 (d, 1H, H-1', $J_{1',2'}$=3.22 Hz), 7.47–8.13 (m, 16H, Bz and H-6), 11.42 (s, 1H, 3-NH).

Method B: with syrup 4b

Using the above procedure, condensation of the 4b syrup (83.8 g) with silylated thymine (prepared from 23 grams of thymine) gave a crude solid that was recrystallized from hot methanol to give a white crystalline product (54.5 g, 60%). The product had the same melting point and ¹H NMR as the product of Method A.

1-(3,5-O-Isopropylidene-β-D-xylofuranosyl)thymine (7)

A suspension of compound 5 (48 g, 85 mmol) in 0.5 M sodium methoxide in methanol (600 mL) was stirred at room temperature overnight. Water (200 mL) was then added to the solution. The mixture was neutralized with acidic resin (Dowex 50, H+ form) and then filtered. The resin was then washed with 80% methanol. The combined filtrate and washings were evaporated in vacuo. The residual aqueous solution was extracted with ethyl acetate (3×200 mL). The aqueous phase was evaporated and co-evaporated with ethanol to give a pale yellow foam (21.3 g, 95.4%) that was pure enough to use as is in the next reaction. An analytical sample of 6 was obtained by crystallization from ethanol to give 6 as white needles. mp 159.1°–160.2° C. (lit. 164°–165° C.). $[\alpha]_D^{23}$ −20.0° (c, 0.55, methanol) $^1$H NMR (DMSO-d$_6$)δ1.76 (s, 3H, CH$_3$), 3 69 (m, 2H, H-5'), 3.94 (m, 3H, H-2',3',4'), 4.72 (t, 1H, 5'-OH, J$_{5'-OH,5'}$=3.52 HZ, D$_2$O exchangeable), 5.68 (m, 2H, H-1'+2'-OH, D$_2$O exchangeable), 7.65 (s, 1H, H-6), 11.26 (s, 1H, 3-NH, D$_2$O exchangeable). The foam was stirred with a mixture of acetone (200 mL) and 1M HCl in ether (20 mL) at room temperature overnight. Molecular sieves (4Å, 15 g) were added and stirring was continued for a further 2 hours to complete the reaction. Molecular sieves were removed by filtration and washed with acetone. The combined filtrate and washings were neutralized with basic resin (Amberlite IR 45) and then evaporated in vacuo to give 7 as a pale yellow syrup (16.17 g), which was crystallized from methanol to give white needles, 23.5 g (95%). mp 182.5°–184° C.; UV (methanol)=λ$_{max}$ 267.3 nm λ$_{min}$ 234.5 nm; $^1$H NMR (DMSO-d$_6$) δ1.26, 1.43 (s, 2×3H, isopropylidene), 1.76 (d, 3H heterocyclic CH$_3$, J$_{CH3,6}$=0.88 HZ), 3.96–4.27 (m, 5H, H-2',3',4',5'), 5.66 (s, 1H, H-1'), 5.95 (bs, 1H, 2'-OH, D$_2$O exchangeable), 7.84 (d, 1H, H-6, J$_{6,CH3}$=1.17 HZ), 11.27 (bs, 1H, 3-NH, D$_2$O exchangeable).

1-[3,5-O-Isopropylidene-2-O-(cyanoethylthio)thiocarbonyl-β-D-xylofuranosyl]thymine (8)

Sodium hydroxide (10 N, 21 mL) was added dropwise with stirring to an ice-cooled mixture of compound 7 (17.7 g, 59.3 mmol) and carbon disulfide (35 mL) in DMSO (70 mL). After 30 minutes, 3-bromopropionitrile (21 mL) was added dropwise. The mixture was stirred at room temperature for 2 hours, and then added dropwise into a saturated sodium chloride solution with vigorous stirring. The solution was then extracted with ethyl acetate. The organic phase was washed with water and dried over magnesium sulfate. Evaporation in vacuo gave a yellow syrup (32.2 g), which was dissolved in dry toluene and seeded with previously prepared crystals. The crystalline product was collected by filtration, washed with toluene and dried to give pale yellow needles (17.3 g). The mother liquor was added dropwise in petroleum ether (b.p. 30°–60° C.) with stirring. The precipitates were collected and recrystallized from toluene to give another batch (4 grams). Total yield 21.29 g (84%). An analytical sample was obtained by recrystallization from acetone-ether to form white needles, melting point 166.4°–167.7 ° C.: UV (methanol) λ$_{max}$ 273.5 nm, λ$_{min}$ 238.0 nm. $[\alpha]_D^{24}$ 10.6° (c, 0.6, methanol). $^1$H NMR (CDCl$_3$) δ1.43, 1.49 (s, 2×3H, isopropylidene), 1.96 (d, 3H, heterocyclic CH$_3$; J$_{CH3,6}$=1.1 Hz), 2.85 (t, 2H, H-2''-CH$_2$; J$_{2'',1''}$=6.8 Hz), 3.43 (t, 2H, H-1''-CH$_2$; J$_{1'',2''}$=6.8 Hz). 4.06–4.08 (m, 1H, H-4'), 4.19 (s, 2H, H-5'), 4.51 (m, 1H, H-3'), 5.75 (s, 1H, H-2'), 6.12 (d, 1H, H-1', J$_{1',2'}$=1.1 Hz), 7.87 (d, 1H, H-6, J$_{6,CH3}$=1.1 Hz), 8.76 (bs, 1H, 3-NH). Anal. calcd for C$_{17}$H$_{21}$N$_3$O$_6$S$_2$: C, 47.76; H, 4.95; N, 9.83; S, 15.00. Found: C, 47.69; H, 5.01; N, 9.76; S, 15.06.

1-(3,5-O-Isopropylidene-β-D-2-deoxy-xylofuranosyl)thymine (9)

Method A To a mixture of compound 8 (3.46 g, 8.1 mmol and triethylborane (1 M in hexanes, 10 mL) in dry toluene (50 mL), tris(trimethylsilyl)silane (3 mL, 9.7 mmol) was added dropwise with stirring at room temperature. For the preparation of tris(trimethylsilyl)silane, see H. Bürger and W. Kilian, J. Organometal. Chem., 1969, 18, 299–306. The reaction was continued in a nitrogen atmosphere overnight. TLC (chloroform-methanol, 95:5) indicated that the starting material had completely disappeared and that compound 9 was the sole product. The reaction mixture was evaporated in vacuo to give a gel-like solid, that was partitioned between acetonitrile and hexanes (100 mL each). The acetonitrile layer was washed with hexanes (5×100 mL), and then evaporated and dried in vacuo to give a pale yellow foam (2.78 g) which was crystallized from hot toluene to give 9 as white crystals, 2.37 g (93.3%).

Method B

A mixture of compound 8 (6.3 g, 15 mmol), azobisisobutyronitrile (AIBN) (0.3 g) and tributyltin hydride (8,5 mL) in dry toluene (50 mL) was heated at 90° C. with stirring under a nitrogen atmosphere for 2 hours, cooled to room temperature and filtered through celite. The filter cake was washed with acetone. The combined filtrate and washings were evaporated to dryness and then partitioned between acetonitrile (100 mL) and hexanes (100 mL). The acetonitrile phase was washed with hexanes (5×100 mL) and then evaporated to give a pale yellow syrup (4.98 g) that was crystallized from acetone-hexanes to give white needles, 3.59 g (86.3%), mp 169.2°–170.0° C. (lit. 165°–167° C.). UV (methanol) λ$_{max}$266.8 nm, λ$_{min}$234.5 nm. $[\alpha]_D^{24}$-5.5° (c, 0.65 methanol) (lit. $[\alpha]_D^{25}$-11.4° ). $^1$H NMR (CDCl$_3$) δ1.38, 1.48 (s, 2×3H, isopropylidene), 1.95 (s, 3H, heterocyclic CH$_3$), 2.07–2.75 (m, 2H, H-2'), 3.81 (m, 1H, H-4') 4.18 (s, 2H, H-5'), 4.44 (m, 1H, H-3'), 6.16 (d, 1H, H-1'J$_{1',2'}$=7.69 Hz), 7.99 (s, 1H, H-6), 8.72 (bs, 1H, 3-NH). Anal. Calcd. for C$_{13}$H$_{18}$N$_2$O$_5$: C, 55.31; H, 6.43; N, 9.93. Found: C, 55.29; H, 6.43; N, 9.88.

1-β-D- (Deoxy-xylofuranosyl)thymine (10)

A solution of compound 9 (22.4 g, 79 mmol) in 5% trifluoroacetic acid in methanol (500 mL) was heated under reflux for 6 hours, cooled to room temperature, and then neutralized with basic resin (Amberlite IR 45). The resin was removed by filtration and washed with aqueous methanol. The combined filtrate and washings were evaporated to dryness. Acetone was added to initiate crystallization. Compound 10 was obtained as white crystals from methanol, 15.8 g (82.6%). mp 168.8°–170.2° C. (lit. 170°–171° C.), $[\alpha]_D^{24}$-8.6° (c, 0.5 methanol) $[\alpha]^{23}_D$ 7.9 (c, 0.68, water) (lit $[\alpha]^{25}_D$ 12° (c, 0.36, water) $^1$H NMR (DMSO-d$_6$) 1.77 (d, 3H, CH$_3$, J$_{CH3,6}$=0.88 Hz), 1.91–2.00, 2.40–2.71 (m, 2H, H-2'), 3.61–3.88 (m, 3H, H-4' and 5'), 4.25 (m, 1H, H-3'), 4.70 (bs, 1H, H-5'-OH, D$_2$O exchangeable), 5.23 (bs, 1H, H-3'-OH, D$_2$O exchangeable), 6.05 (dd, 1H, H-1', J=2.64 Hz, 8.20 Hz), 7.80 (d, 1H, H-6, J$_{6,CH3}$=0.87

Hz), 11.16 (bs, 1H, 3-NH, D$_2$O exchangeable). Anal. Calcd. for C$_{10}$H$_{14}$N$_2$O$_5$: C, 49.58; H, 5.83; N, 11.57. Found: C, 49.50; H, 5.85; N, 11.51.

1-(5-O-Trityl-3-O-mesyl-β-D-2-deoxy-xylofuranosyl)thymine (12)

Trityl chloride (16.4 g, 58.7 mmol) was added portionwise to a solution of compound 10 (12.9 g, 53.3 mmol) and triethylamine (5.9 mL) in dry pyridine (50 mL). The mixture was stirred at room temperature for 48 hours. TLC (chloroform-methanol, 95:5) showed that the reaction had been completed. The mixture was cooled in an ice-water bath and then mesyl chloride (20.1 mL) was added dropwise. The mixture was stirred at room temperature overnight and then poured into a mixture of ice and water with stirring. The precipitate was collected by filtration, washed with water thoroughly and dried in vacuo at 50° C. to give a tan solid (32.9 g). An analytical sample was prepared by preparative TLC (chloroform-methanol, 96:4). $^1$H NMR (CDCl$_3$)=δ1.80 (d, 3H, heterocyclic CH$_3$, J$_{CH3,6}$=0.66 Hz), 2.30-2.91 (m, 2H, H-2'), 2.75 (S, 3H, CH$_3$SO$_2$), 3.23-3.74 (m, 2H, H-5'), 4.10-4.27 (m, 1H, H-4'), 5.21-5.31 (m, 1H, H-3'), 6.25 (dd, 1H, H-1', J=3.52, 7.69 Hz), 7 25-7.50 (m, 16H, H-6 and trityl), 8.63 (bs, 1H, 3NH).

1-(5-O-Trityl-3-azido-β-D-2,3-deoxyribofuranosyl)thymine (13)

A solution of compound 12 (32 g, 56.9 mmol) in dry dimethylformamide (200 mL) was treated with sodium azide (15 g) at 90° C. with stirring for 3 hours. The mixture was cooled to room temperature and added dropwise into water with stirring. The precipitate was collected by filtration, washed with water and dried to give a pale yellow powder (27.5 g, 95%). An analytical sample was prepared by preparative TLC (chloroform-methanol, 95:5). IR (KBr) (cm$^{-1}$): 2104.6, (azido) . $^1$H NMR (CDCl$_3$)=δ1.52 (d, 3H, heterocyclic CH$_3$, J$_{CH3,6}$=1.09 Hz), 2.36-2.53 (m, 2H, H-2'), 3.45 (qd, 2H, H-5', J=3.08, 10.77 Hz), 3.92-4.03 (m, 1H, H-4'), 4.27-4.43 (m, 1H, H-3'), 6.25 (t, 1H, H-1', J$_{1',2'}$=6.25 Hz), 7.25-7.55 (m, 16H, H-6 and trityl), 8.59 (bs, 1H, 3-NH).

3'-Azido-3'-deoxythymidine (14)

A solution of 13 (27 g, 53 mmol) in 80% acetic acid (300 mL) was heated under reflux for 2 hours. TLC (chloroform-methanol, 95:5) showed the starting material had disappeared. Water (180 mL) was added. The mixture was treated with active charcoal, filtered and washed with water. The combined filtrate and washings were evaporated to give a syrup, which was dissolved in water 150 mL) and extracted with hexanes (4×100 mL). The aqueous phase was evaporated in vacuo to give a pale yellow foam (12.5 g), which was crystallized from hot water. An analytical sample was obtained from two recrystallizations from water, that was identical to an authentic sample. mp 120.7°-122.2° (lit. 120°-122° C.). UV (water) λ$_{max}$ 266.5 nm, λ$_{min}$ 234.5 nm. IR (KBr) (cm$^{-1}$): 2087.24 (azido). $^1$HNMR (DMSO-d$_6$)=δ1.78 (d, 3H, heterocyclic CH$_3$, J$_{CH3,6}$=0.88 Hz), 2.24-2.41 (m, 2H, H-2'), 3.57-3.67 (m, 2H, H-5'), 3.79-3.85 (m, 1H, H-4'), 4.27-4.50 (m, 1H, H-3'), 5.18 (t, 1H, 5'-OH, J$_{5'-OH,5'}$=5.27 Hz, D$_2$O exchangeable). 7.67 (d, 1H, H-6, J$_{6,CH3}$=1.17 Hz), 11.27 (bs. 1H, 3-NH, D$_2$O exchangeable).

EXAMPLE 2
Process for the Preparation of 3'-Azido-2', 3'-Dideoxyuridine

Figure 2A:
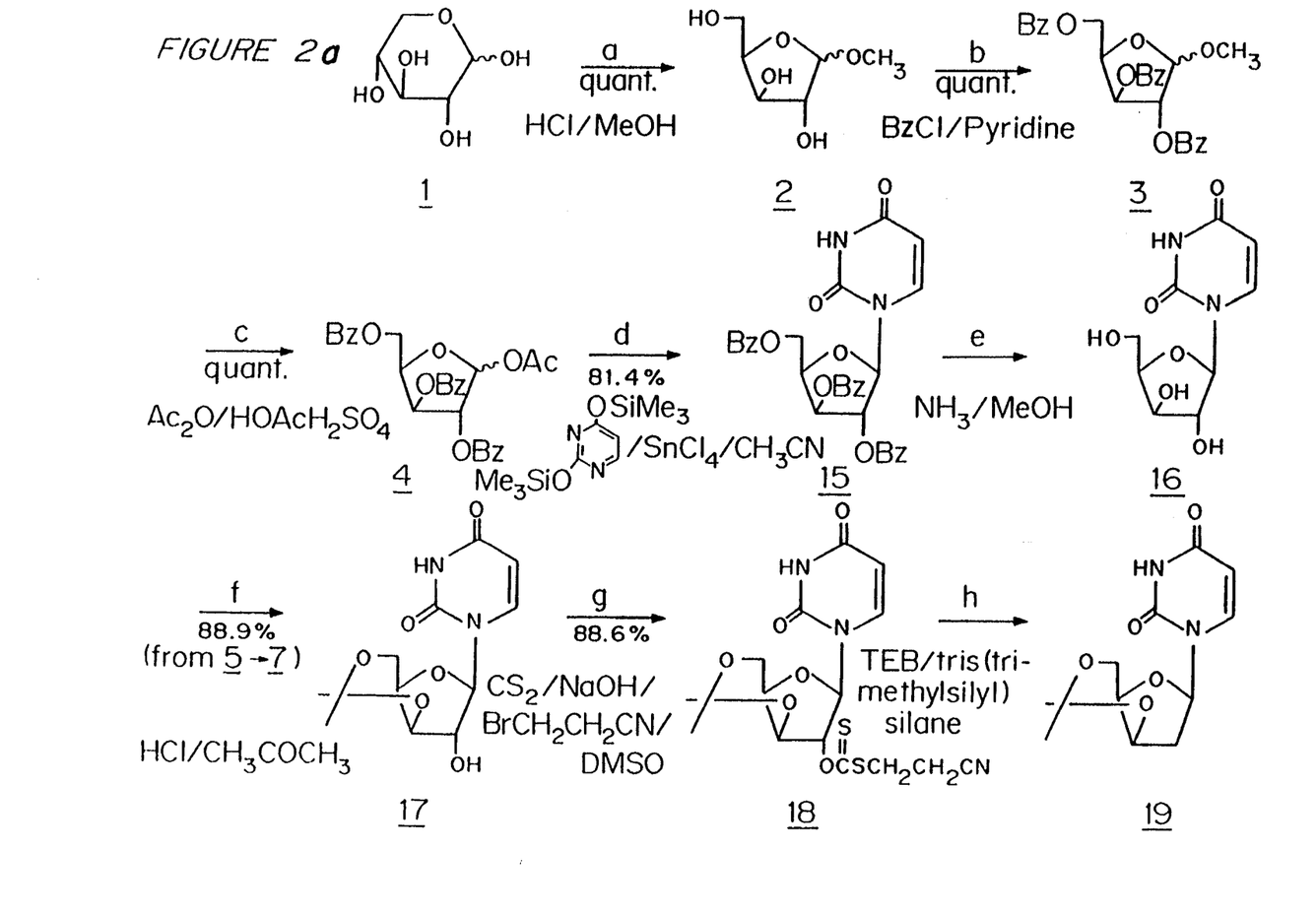
Figure 2B:
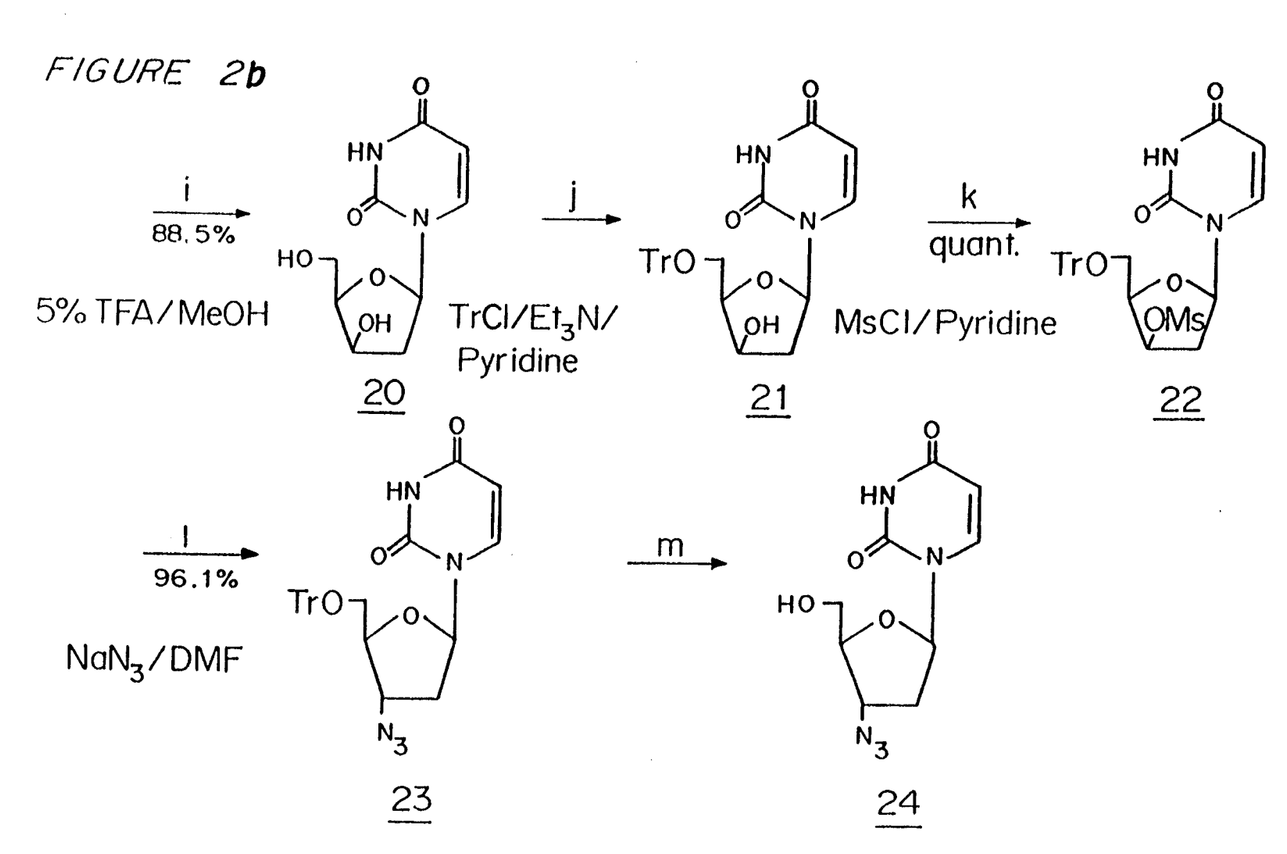

FIG. 2 is an illustration of a process for the preparation of 3'-azido-2',3'-dideoxyuridine from xylose in which the 2'-hydroxyl group is removed by reductive elimination of a 2'-O-(cyanoethylthio)thiocarbonyl group. The process is similar to that described above for 3'-azido-3'-deoxythymidine.

1- (2,3,5-Tribenzoyl-β-D-xylofuranosyl)uracil (15)

To an ice-cooled solution of 4b (146.05 g, corresponding to 0.283 mole of xylose) in dry acetonitrile (1 liter) was added tin (IV) chloride (40 mL). Silylated uracil (prepared from 44 grams of uracil) was then added dropwise with stirring. After stirring at room temperature for 48 hours, the reaction mixture was neutralized with a mixture of ice and solid sodium bicarbonate and then filtered. The filter cake was washed with acetonitrile. The combined filtrate and washings were evaporated to give a pale yellow syrup which was dissolved in ethyl acetate (1 liter) and washed with water. The organic phase was dried over anhydrous sodium sulfate and evaporated to give a pale yellow syrup which was crystallized from hot methanol to give 15 as white fine crystals, 127.8 g (81.4%); melting point 119.0°-120.5° C. (lit. 112°-118° C.). [α]$^{24}$D+76.48° (c, 0.81, chloroform) (lit. [α]$^{24}$$_D$+75°, c 0.8, CHCl$_3$). $^1$H NMR (CDCl$_3$). $^1$H NMR (CDCl$_3$) δ4.71-4.92 (m, 3H, H-4 'and 5'), 5.64-5.89 (m, 3H, H-2',3' and 5), 7.26-8.13 (m, 16H, Bz and H-6), 8.87 (br s, 1H, 3-NH).

1-(3,5-O-Isopropylidene-β-D-xylofuranosyl)uracil (17)

A suspension of 15 (127.8 g) in saturated methanolic ammonia (1 liter) was stirred at room temperature for 48 hours. Solvent was removed in vacuo to give 16 as a pale yellow syrup. An analytical sample of 16 was prepared by preparative TLC (chloroform-methanol, 8:2), mp 158.3°-159.5° C. (lit. 156°-157° C.), [α]$^{24}$D+20.28° (c 0.51, water) (lit. [α]$^{24}$D +29°) (c 0.4, water), $^1$H NMR (DMSO-d$_6$), 3.65-3.80 (m, 2H, H-5') 3.90-4.20 (m, 3H, H-2', 3' and 4'), 4.71 (t, 1H, 5'-OH, D$_2$O exchangeable, J$_{5'-OH,5'}$=5.3 H$_z$), 5.39 (d, 1H, 3'-OH, D$_2$O exchangeable, J$_{3'-OH,3'}$=3.2 H$_z$), 5.57-5.75 (m, 3H, H-1',5 and 2'-OH, D$_2$O exchangeable), 7.80 (d, 1H, H-6, J$_{6,5}$=8.2 H$_z$), 11.26 (brs, 1H, 3-NH, D$_2$O exchangeable). The syrup was stirred with a mixture of acetone (500 mL) and 1 M HCl in diethyl ether (50 mL) at room temperature overnight and then stored in a refrigerator for another 24 hours. The resulting solid product was collected by filtration, washed with acetone until neutral, and then dried to give 17 as a white powder 56 g (88.9%); melting point 266°-268° C. (lit.[4] 264°-266° C.). $^1$H NMR (DMSO-d$_6$) δ1.30 (s, 3H, CH$_3$), 1.55 (s, 3,H CH$_3$), 3.90-4.30 (m, 5H, H-2', 3', 4' and 5'), 5.57 (m, 2H, H-1' and 5), 5.97 (d, 1H, 2'-OH, D$_2$O exchangeable, J$_{2'-OH,2'}$=4.4 H$_z$), 7.95 (d, 1H, H-6, J$_{6,5}$=8.2 H$_z$), 11.28 (brs, 1H, 3-NH, D$_2$O exchangeable).

1-[3,5-O-Isopropylidene-2-O-(cyanoethylthio)thiocarbonyl-β-D-xylofuranosyl]uracil (18)

Sodium hydroxide (10 N, 50 mL) was added dropwise with stirring to a mixture of 17 (55 g, 193 mmol) and carbon disulfide (90 mL) in DMSO (200 mL). After 30 minutes, 3-bromopropionitrile (80 g, 50 mL) was added. The mixture was stirred at room temperature for 4 hours, and poured into a saturated sodium chloride solution with vigorous stirring. The resulting solid was collected by filtration, dissolved in ethyl acetate, washed with water, and dried over anhydrous sodium sulfate. Evaporation in vacuo gave 18 as a pale yellow syrup (70.7 g, 88.6%). Crystallization from 95% ethanol gave white needles, mp 179.8°–181.3° C. $[\alpha]^{24}D+31.65°$ (c 0.53, methanol), UV (methanol): $\lambda_{max}$ 273.4 nm, $\lambda_{min}$ 237.0 nm, IR (KBr) (cm$^{-1}$) 2250 (w, CN), $^1$H NMR (CDCl$_3$) $\delta$1.40 (s, 3H, CH$_3$), 1.48 (s, 3H, CH$_3$), 2.86 (t, 2H, H-2''-CH$_2$, $J_{2'',1''}$=6.7 Hz), 3.44 (t, 2H, H-1''-CH$_2$, $J_{1'',2''}$=6.7 Hz), 4.13–4.21 (m, 3H, H-4' and 5'), 4.49 (m, 1H, H-3'), 5.72–5.81 (m, 2H, H-2' and 5, $J_{5,6}$=7.9 Hz) 6.07 (s, 1H, H-1'), 8.04 (d, 1H, H-6, $J_{6,532}$ 8.2 Hz), 8.89 (brs, 1H, 3-NH) Anal. calcd for C$_{16}$H$_{19}$N$_3$O$_6$S$_2$: C, 46.48; H, 4.63; N, 10.15; S, 15.51. Found: C, 46.58; H, 4.64; N, 10.08; S, 15.41.

1-(3,5-O-Isopropylidene-$\beta$-D-2-deoxy-xylofuranosyl)uracil (19)

Method A

To a mixture of compound 18 (1.2 g, 3 mmol) and triethylborane (1 M in hexanes, 3.8 mL) in dry toluene (20 mL), tris(trimethylsilyl)silane (1.2 mL, 3.6 mmoL) is added dropwise with stirring at room temperature. The reaction mixture is stirred under nitrogen atmosphere overnight, and then evaporated in vacuo to give a crude product, that is partitioned between acetonitrile and hexanes. The acetonitrile layer is washed with hexanes, and then evaporated to give a syrup which is crystallized from hot toluene to give white crystals of 19.

Method B

A mixture of 18 (75 g, 181 mmol) and azobisisobutyronitrile (AIBN) (4 g) in dry toluene (500 mL) was heated at 100° C. with stirring under a nitrogen atmosphere. Tri-n-butyltin hydride (80 mL) was added dropwise and heating was continued for 1.5 hours. The solution was then cooled to room temperature and filtered. The resulting brown cake was washed with acetonitrile. The combined filtrates were evaporated in vacuo to give a pale yellow solid. This crude product was dissolved in acetonitrile (1.52 L) and washed with hexanes (5×800 mL). The acetonitrile phase was then evaporated and the resulting syrup was dried in vacuo to give pale yellow crystals that were recrystallized from acetone-hexanes to give 19 as a white prism: 40 g (82.6%), mp 154.3°–155.3° C. $[\alpha]^{23}D+44.04°$ (c 0.57, methanol), UV (water) $_{max}$ 262.9 nm, $_{min}$ 231.0 nm. $^1$H NMR (CDCl$_3$) $\delta$1.36 (s, 3H, CH$_3$), 1.46 (s, 3H, CH$_3$), 2.13–2.74 (m, 2H, H-2'), 3.82–3.88 (m, 1H, H-4'), 4.19 (s, 2H, H-5''), 4.41–4.49 (m, 1H, H-3'), 5.70 (d, 1H, H-5, $J_{5,6}$=8.13 Hz), 6.09 (dd, 1H, H-1', J=1.1 Hz, 7.25 Hz), 8.12 (d, 1H, H-6, $J_{6,5}$=8.13 Hz), 8.95 (brs, 1H, 3-NH). Anal., calcd for C$_{12}$H$_{16}$N$_2$O$_5$: C, 53.72; H, 6.01; N, 10.45. Found: C, 53.47; H, 6.05; N, 10.35.

1-$\alpha$-D-(2-Deoxy-xylofuranosyl)uracil (20)

A solution of 1.9. (40 g) in 5% trifluoroacetic acid in methanol (600 mL) was heated under reflux for 6 hours. Evaporation of the solvent and co-evaporation with ethanol gave white crystals that were collected by filtration, washed with acetone, and then dried in vacuo to give 20 (26.6 g). The combined mother liquor and washings were evaporated to dryness, the residue was dissolved in water and extracted with ethyl acetate. The neutral aqueous phase was evaporated and the residue was crystallized from ethanol to give additional product (3.5 g). Total yield of 10 was 30.1 g (88.5%). mp 166.9°–167.9° C. (lit.[5,6] 160°–162° C., 165°–166° C.), $[\alpha]^{24}D+44.65°$ (c 0.52, water) (lit.[6] $[\alpha]^{22}D+40$ (c 1.4, water), $^1$H NMR (DMSO-d$_6$), $\delta$1.75–1.95, 2.40–2.75 (m, 2H, H-2'), 3.56–3.86 (m, 3H, H-4' and 5'), 4.25 (m, 1H, H-3'), 4.67 (t, 1H, 5'-OH, D$_2$O exchangeable, $J_{5=OH,5'}$=5.57 Hz), 5.23 (d, 1H, 3'-OH, D$_2$O exchangeable, $J_{3'-OH,3'}$=3.23 Hz), 5.65 (d, 1H, H-5, $J_{5,6}$=7.91 Hz), 6.05 (dd, 1H, H-1', J=1.76 Hz, 5.15 Hz), 7.90 (d, 1H, H-6, $J_{6,5}$=7.91 Hz), 11.20 (brs, 1H, 3-NH, D$_2$O exchangeable.).

1-(5-O-Trityl-3-O-mesyl-$\beta$-D-2-deoxy-xylofuranosyl)uracil (22)

Trityl chloride (13.66 g, 53.8 mmol) was added portionwise to a solution of 20 (10 g, 48.9 mmol) and triethylamine (6.5 mL) in dry pyridine (200 mL). The mixture was heated under reflux for 8 hours. TLC (chloroform-methanol, 95:5) indicated that the starting material had almost completely disappeared. The solution was then cooled in an ice-water bath, and mesyl chloride (12.2 mL, 0.16 mol) added dropwise with stirring. The reaction mixture was stirred at room temperature overnight, and then poured into a mixture of ice water (4 liters). The precipitate was collected by filtration, washed with water, and then dried to give 22 as a pale yellow powder 25.87 g (quant.).

Analytical samples of 21 and 22 were prepared by short vacuum flash silica gel column chromatography. Compound 21 was eluted with chloroform-methanol (95:5). The desired fraction was crystallized from acetone to give pale yellow needles, melting point. 225°–228° C. (lit. 230°–231° C.). Compound 22 was eluted first with chloroform and then with chloroform-methanol (95:5). The desired fraction was crystallized from acetone-hexanes to give pale yellow needles. m.p. 154.6° C. (dec) (lit. 152°–155° C. (dec)) $^1$H NMR (CDCl$_3$) $\delta$2.35–2.75 (m, 2H, H-2'), 2.77 (s, 3H, CH$_3$SO$_2$), 3.28–3.73 (m, 2H, H-5'), 4.13–4.35 (m, 1H, H-4'), 5.21–5.35 (m, 1H, H-3'), 5.64 (d, 1H, H-5, $J_{5,6}$=6.98), 6.20 (dd, 1H, H-1', J=3.08 Hz, 7.36 Hz), 7.22–7.51 (m, 16H, H-6 and trityl) 8.80 (brs, 1H, 3-NH).

1-(5-O-Trityl-3-azido-$\beta$-D-2,3-deoxyribofuranosyl)uracil (23)

A solution of 22 (25.87 g, 47.2 mmol) and sodium azide (13.32 g, 0.205 mol) in dry dimethylformamide (200 mL) was stirred at 80°–90° C. for 3 hours. The mixture was cooled at room temperature and then poured into water (3 liters) with vigorous stirring. The precipitate was collected by filtration, washed with water, and dried to give 23 as a pale yellow powder (22.44 g, 96.1%), that was crystallized from ethanol to give pale yellow needles, melting point 174.0°–175.5° C. (lit. 175°–176° C.). IR (KBr) (cm$^{-1}$): 2102.68 (azido) $^1$H NMR (CDCl$_3$) $\delta$2.35–2.53 (m, 2H, H-2'), 3.45–3.52 (m, 2H, H-5'), 3.85–4.05 (m, 1H, H-4'), 4.33 (m, 1H, H-3'), 5.40 (d, 1H, 5-H, $J_{5,6}$=7.80 Hz), 6.20 (t, 1H, H-1', $J_{1',2'}$=5.70 Hz 7.20–7.60 (m, 15H, trityl), 7.31 (d, 1H, H-6, $J_{6,5}$=8.10 Hz), 8.88 (brs, 1H, 3-NH).

1-(3-Azido-$\beta$-D-2,3-deoxyribofuranosyl)uracil (24)

A suspension of 23 (11.7 g, 23.6 mmol) in 80% acetic acid (100 mL) was heated under reflux for 20 min., and then water (20 mL) was added. The resulting trityl alcohol was removed by filtration. The filter cake was washed with water. The combined filtrate and washings were treated with active charcoal then evaporated in vacuo to give yellow solid (4.68 g, 77.8%). Recrystallization from methanol gave white crystals which were identical to an authentic sample. mp 174.0°–175.5° C. (lit. 175°–176° C.) $^1$H NMR (DMSO-$d_6$) $\delta$2.27–2.48 (m, 2H, H-2'), 3.62 (m, 2H, H-5'), 3.78–3.91 (m, 1H, H-4'), 4.30–4.47 (m, 1H, H-3'), 5.18 (bs, 1H, 5'-OH, D$_2$O exchangeable), 5.63 (d, 1H, H-5, $J_{5,6}$=7.91 Hz), 6.07 (t, 1H, H-1, $J_{1,2}$=6.44 Hz), 7.82 (d, 1H, H-6, $J_{6,5}$=7.91 Hz), 11.31 (bs, 1H, 3-NH, D$_2$O exchangeable).

This invention has been described with reference to its preferred embodiments. Variations and modifications of the deoxygenation of nucleosides will be obvious to those skilled in the art from the foregoing detailed description of the invention. It is intended that all of these variations and modifications be included within the scope of the appended claims.

We claim

1. A process for the deoxygenation of one or both of the 2'- or 3'-hydroxyl groups of a nucleoside without N-alkylation of the heterocyclic base of said nucleoside comprising:
    protecting hydroxyl groups on the nucleoside that are not to be deoxygenated;
    reacting the unprotected hydroxyl groups in base with carbon disulfide and a 3-haloprionononitrile of the formula XCH$_2$CH$_2$CN or a 2-nitroethylhalide of the formula XCH$_2$CH$_2$NO$_2$, wherein X is chloro, bromo, or iodo, to form a 2' or 3'-O-(cyanoethylthio or nitroethylthio)thiocarbonyl; and then
    reductively eliminating the (cyanoethylthio or nitroethylthio)thiocarbonyl to a 2' or 3'-hydrogen moiety.

2. The process of claim 1 wherein the protected nucleoside is reacted with 3-halopropionitrile.

3. The process of claim 1 wherein the protected nucleoside is reacted with 2-nitroethylbromide.

4. The process of claim 1 wherein the 2'-position is deoxygenated.

5. The process of claim 4 wherein the protected nucleoside is a 1-(3,5-O-protected-$\beta$-D-xylofuranosyl)uracil.

6. The process of claim 4 wherein the protected nucleoside is a 1-(3,5-O-protected-$\beta$-D-xylofuranosyl)thymine.

7. A process for the deoxygenation of the 2'-hydroxyl group of a 1-($\beta$-D-xylofuranosyl)purine or pyrimidine nucleoside without N-alkylation of the heterocyclic base of said nucleoside comprising:
    protecting the 3' and 5'-hydroxyl groups with an alkylidene;
    converting the nucleoside to a 1-[3,5-O-alkylidene-2-O-(cyanoethylthio or nitroethylthio)thiocarbonyl-$\beta$-D-xylofuranosyl]purine or pyrimidine; and
    reducing the cyanoethylthio or nitroethylthio product to form a 1-(3,5-O-alkylidene-$\beta$-D-2-deoxyxylofuranosyl)purine or pyrimidine.

8. The process of claim 7 wherein the reduction is accomplished with tri-n-butyltin hydride and azobisisobutyronitrile.

9. The process of claim 7 wherein the reduction is accomplished with triethylborane and tris(trimethysilyl)silane.

10. The process of claim 1 wherein the reductive elimination is accomplished with tri-n-butyltin hydride and azobisisobutyronitrile.

11. The process of claim 1 wherein the reductive elimination is accomplished with triethylborane and tris(trimethylsilyl)silane.

12. The process of claim 1 wherein the nucleoside is selected from the group consisting of thymidine, cytidine, uridine, adenosine, inosine, and guanosine.

13. A process for the deoxygenation of a ribose comprising:
    protecting the hydroxyl groups that are not to be deoxygenated;
    reacting the remaining hydroxyl groups in base with carbon disulfide and a 3-haloprionononitrile of the formula XCH$_2$CH$_2$CN or a 2-nitroethylhalide of the formula XCH$_2$CH$_2$NO$_2$, wherein X is chloro, bromo, or iodo, to form a 2' or 3'-O-(cyanoethylthio or nitroethylthio)thiocarbonyl; and then
    reductively eliminating the (cyanoethylthio or nitroethylthio)thiocarbonyl to a hydrogen moiety.

14. A process for the deoxygenation of a xylose comprising:
    protecting the hydroxyl groups that are not to be deoxygenated;
    reacting the remaining hydroxyl groups in base with carbon disulfide and a 3-haloprionononitrile of the formula XCH$_2$CH$_2$CN or a 2-nitroethylhalide of the formula XCH$_2$CH$_2$NO$_2$, wherein X is chloro, bromo, or iodo, to form a 2' or 3'-O-(cyanoethylthio or nitroethylthio)thiocarbonyl; and then
    reductively eliminating the (cyanoethylthio or nitroethylthio)thiocarbonyl to a hydrogen moiety.

15. The compound wherein R and R' are hydrogen or oxygen protecting groups, X is selected from the group consisting of (cyanoethylthio)thiocarbonyl and (nitroethylthio)thiocarbonyl, and B is a purine or pyrimidine base.

16. The compound of claim 15 wherein R and R' together are isopropylidene.

17. The compound of claim 15 wherein X is (cyanoethylthio)thiocarbonyl.

18. The compound of claim 15, wherein B is selected from the group consisting of thymine, uracil, cytosine, adenine, and guanine.

* * * * *